United States Patent [19]

Hung

[11] Patent Number: 5,234,414

[45] Date of Patent: Aug. 10, 1993

[54] AUTOMATICALLY CLOSED DRIPPING APPARATUS FOR INTRAVENOUS ADMINISTRATION

[76] Inventor: Yung-Feng Hung, c/o Hung Hsing Patent Service Center, P.O. Box 55-1670, Taipei, (10477), Taiwan

[21] Appl. No.: 952,332

[22] Filed: Sep. 28, 1992

[51] Int. Cl.$^5$ .............................................. A61M 5/16
[52] U.S. Cl. .................................................. 604/254
[58] Field of Search ............... 604/254, 127, 251, 252, 604/253

[56] References Cited

U.S. PATENT DOCUMENTS

| | | | |
|---|---|---|---|
| 4,449,976 | 5/1984 | Kamen | 604/254 |
| 4,731,060 | 3/1988 | Catalano | 604/254 |
| 4,870,987 | 10/1989 | Cheng | 604/254 X |

Primary Examiner—John D. Yasko

[57] ABSTRACT

A dripping apparatus for intravenous administration includes: an intravenous container filled with a medical liquid in the container, a reservoir connected to the intravenous container having a diaphragm formed in a lower portion of the reservoir, a delivery tube connected to the reservoir for directing the medical liquid from the container and the reservoir to an injection needle or cannula into a patient's body through a dripping flow rate adjuster, and a floatable valve slidably held in the diaphragm in the reservoir, in which the valve is operatively floated to open a valve opening in the diaphragm by the liquid in the reservoir for performing the dripping operation and upon an exhausting or empty in the reservoir, the valve will gravitationally descend to close the valve opening for preventing air entrance into the needle and preventing a backflow of a patient's blood to clog the needle.

4 Claims, 2 Drawing Sheets

AUTOMATICALLY CLOSED DRIPPING APPARATUS FOR INTRAVENOUS ADMINISTRATION

BACKGROUND OF THE INVENTION

In administering a medical liquid into a patient's body through an intravenous (I.V.) dripping system, it should be very carefully to always monitor the dripping liquid level in the I.V. container or bag, easily causing fatigue to a nurse or a patient's companion. It may be inadvertently cared to empty the I.V. liquid in the administering dripping system especially when tired or sleepy at night time, thereby causing a backflow of the patient's blood into the needle or delivery tube of the dripping system having air enterring therein and the backflow blood may coagulate to clog the needle from administering I.V. liquid. The clogged needle or cannula should be replaced with a new one and an intravenous injection spot on the patient's skin or body should be repeatedly searched causing inconvenience for a nurse and also sticking injury to the patient.

SUMMARY OF THE INVENTION

The object of the present invention is to provide a dripping apparatus for intravenous administration including: an intravenous container filled with a medical liquid in the container, a reservoir connected to the intravenous container having a diaphragm formed in a lower portion of the reservoir, a delivery tube connected to the reservoir for directing the medical liquid from the container and the reservoir to an injection needle or cannula into a patient's body through a dripping flow rate adjuster, and a floatable valve slidably held in the diaphragm in the reservoir, in which the valve is operatively floated to open a valve opening in the diaphragm by the liquid in the reservoir for performing the dripping operation and upon an exhausting or empty in the reservoir, the valve will gravitationally descend to close the valve opening for preventing air entrance into the needle and preventing a backflow of a patient's blood to clog the needle.

DETAILED DESCRIPTION

Figure 1:
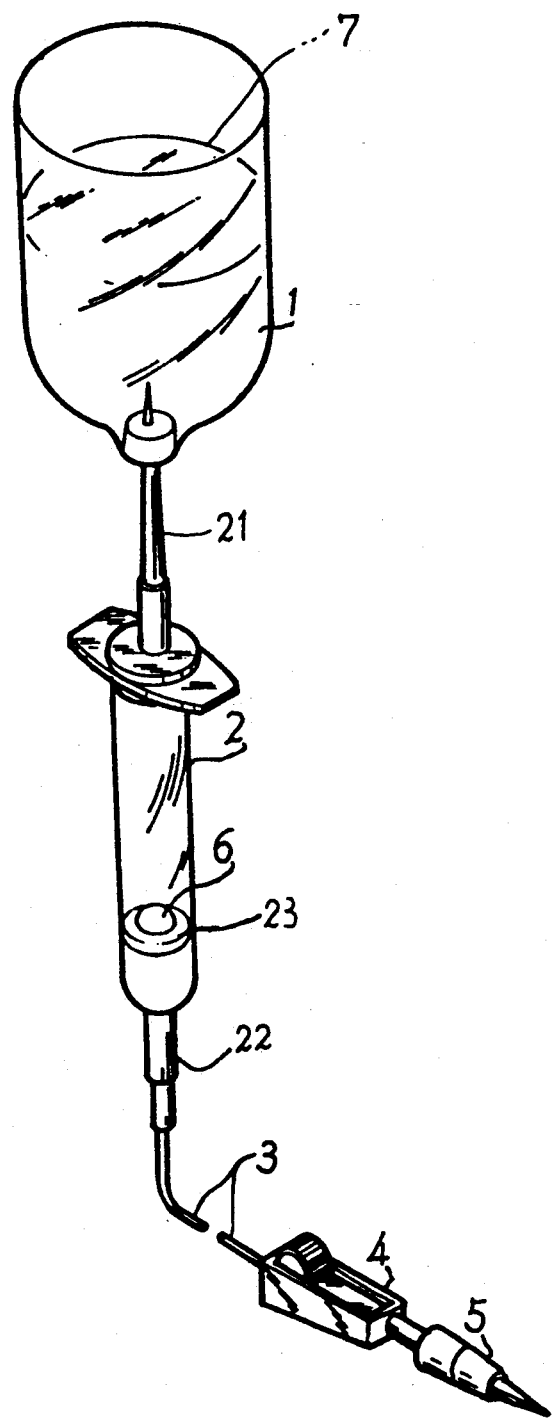
FIG. 1 is a perspective view of the present invention.

As shown in FIGS. 1-4, the present invention comprises: an intravenous container or bag 1 filled with medical liquid, infusion blood, water or any other intravenous administering liquid 7 therein, a reservoir 2, a delivery tube 3, a flow rate adjuster 4, an injection needle or cannula 5, and a floatable valve 6 slidably held in the reservoir 2.

The reservoir 2 includes: an upper adapter 21 upwardly connected to the intravenous container 1 for directing therein the medical liquid 7 in the container 1, a lower adapter 22 connected to the delivery tube 3 for downwardly discharging the liquid into the tube 3, a diaphragm 23 formed in a lower portion of the reservoir 2 separating an upper chamber 24 formed in an upper portion of the reservoir and a lower chamber 25 positioned in a lower portion of the reservoir 2.

The diaphragm 23 is formed with a central valve opening 231 in the central portion of the diaphragm and a valve seat 232 formed on the diaphragm 23 disposed around the opening 231 and engageable with the valve 6 for closing the opening 231.

The floatable valve 6 may be made of materials having enough buoyancy floatable in the reservoir 2 for opening the valve opening 231 when the reservoir 2 having a liquid flowing through the opening 231 and keeping a liquid level in the upper chamber 24 above the diaphragm 23 in the reservoir 2, and the valve 6 will gravitationally descend to downwardly close the opening 231 in the disphrgam 23 when the reservoir 2 is empty without having liquid 7 therein.

The floatable valve 6 is preferably integrally formed and made of foam materials selected from silicon rubber foam, or any other foam materials having a plurality of cells or void spaces in the valve 6 to have an enough buoyancy floatable in the reservoir 2 whenever having a liquid level therein.

The float valve 6 may also be made as a hollow body floatable in the reservoir 2 when having a liquid level in the reservoir 2.

The floatable valve 6 includes: an upper valve portion 61 slidably held in the upper chamber 24 above the diaphragm 23 of the reservoir 2, a lower valve portion 62 slidably held in the lower chamber 25 below the diaphragm 23, a stem 63 having a height larger than a thickness of the diaphragm 23 connecting the upper valve portion 61 and the lower valve portion 62 and slidably held in the valve opening 231 in the diaphragm 23, and a Passage (64, 65) formed in the stem 63 and in the lower valve Portion 62 when floatably opening the valve 6 for directing medical liquid 7 downwardly through the passage towards the lower chamber 25 and the delivery tube 3 connected to the needle 5.

The passage of the valve 6 includes a vertical slot 64 longitudinally formed through (or in) the stem 63 of the valve 6 and a horizontal groove 65 transversely recessed in an upper surface 621 of the lower valve portion 62 and communicating the vertical slot 64 in the stem 63, with the vertical slot 64 being ended its upper slot end 641 adjacent to and without upwardly exceeding a bottom surface 611 of the upper valve portion 61.

The upper valve portion 61 has a volume and a weight greater than that of the lower valve portion 62 to ensure a gravitational descending of the valve 6 downwardly for closing the valve opening 231 when the upper chamber 24 has no liquid level existing therein for floating the upper valve portion 61.

Although the shapes of the upper and lower valve portions 61, 62 are not limited in this invention, each valve portion is preferably formed as semi-spherical, or mushroom shaped with the upper valve portion 61 arcuately tapered upwardly and with the lower valve portion 62 arcuately tapered downwardly as shown in the figures. Other shapes such as shallow cylindrical, conical, elliptical or even spherical shapes may also be used.

Figures 2, 3, 4:
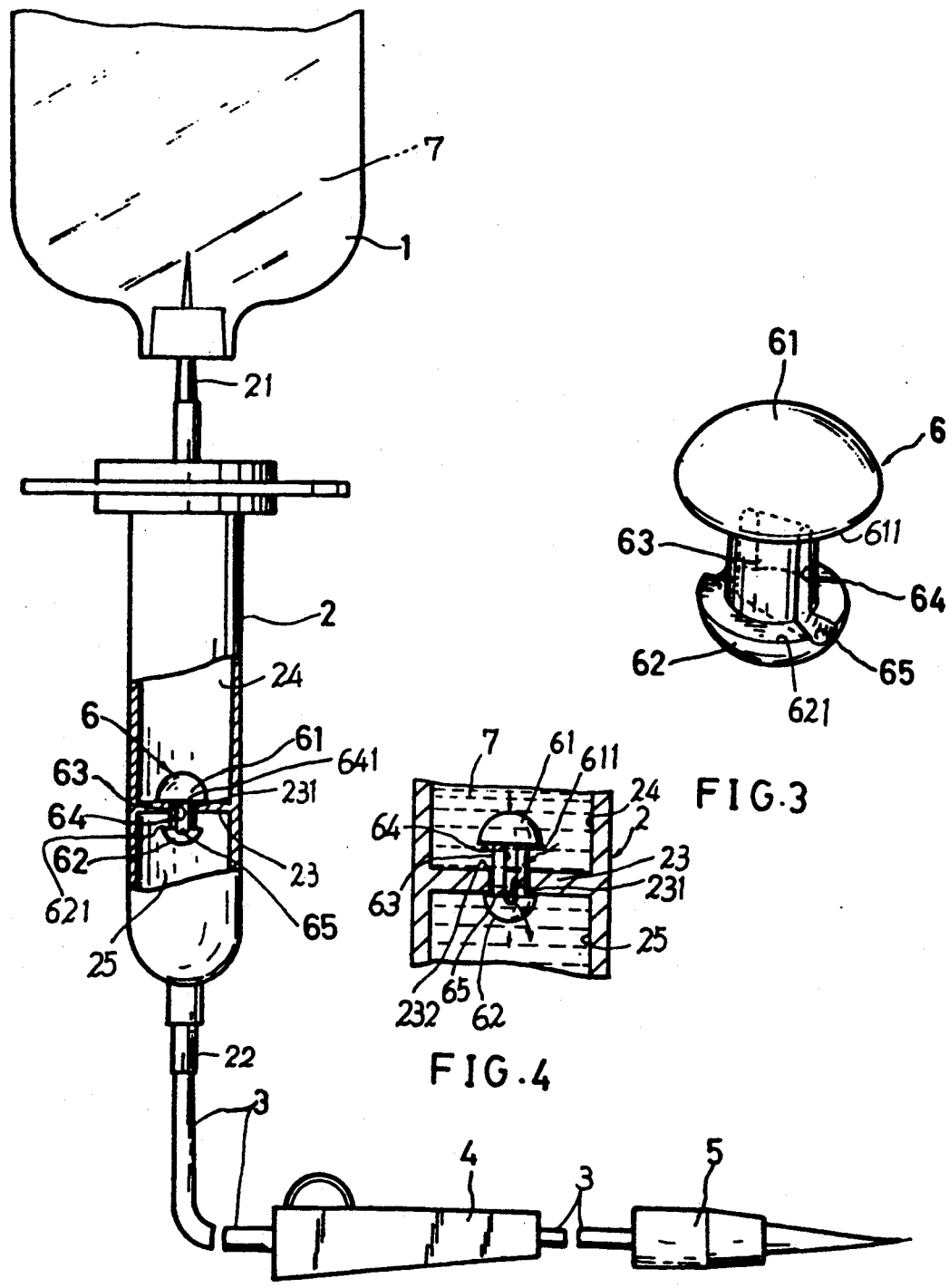
FIG. 2 is a partial sectional drawing of the present invention.
FIG. 3 is a perspective view of the floatable valve of the present invention.
FIG. 4 is an illustration showing a floating and opening of the valve, allowing a flow of the dripping liquid in accordance with the present invention.

In using the present invention for intravenous administration, the medical liquid 7 in the container 1 is downwardly drained into the upper chamber 24 of the reservoir 2 for first floating the upper valve portion 61 as shown in Figure 4, and the buoyancy of the valve 6 will raise the lower valve portion 62 upwardly to be retained on a bottom surface of the diaphragm 23 for limiting an upwardly floating movement of the valve 6. The liquid 7 is then directed downwardly through the vertical slot 64 and the horizontal groove 65 into the lower chamber 25 for a downwardly continuous flow of the liquid into the delivery tube or hose 3 for administering use through the needle 5 inserted into a patient's body.

When the liquid is empty in the container 1 and the upper chamber 24 of the reservoir 2, and even the lower chamber 25 is still full with liquid level having a tendency for floating the lower valve portion 62 upwardly, the gravitational force (weight) of the upper valve portion 61 is greater than the buoyancy of the lower valve portion 62 so that the whole valve 6 will gravitationally descend to close the valve opening 231 in the diaphragm 23, precluding the air enterring into the delivery tube 3 and the needle 5 for preventing a backflow of the patient's blood, beneficial for a patient's health and also for a better nurse care.

The diameter of the stem 63 of the valve 6 is preferably slightly smaller than a diameter of the valve opening 231 for a smooth reciprocative opening or closing operation of the valve 6 held in the opening 231 of the diaphragm.

I claim:

1. A dripping apparatus for intravenous administration comprising: an intravenous container filled with a medical liquid in the container, a reservoir upwardly connected to the intravenous container having a diaphragm formed in a lower portion of the reservoir, a delivery tube upwardly connected to the reservoir for directing the medical liquid from the container and the reservoir to an injection needle inserted into a patient's body through a dripping flow rate adjuster, and a floatable valve slidably held in the diaphragm in the reservoir, in which the valve is operatively floated to open a valve opening in the diaphragm by the liquid in the reservoir for performing the dripping administration operation; and upon an empty in the reservoir, the valve will gravitationally descend to close the valve opening for preventing air entrance into the needle and preventing a backflow of a patient's blood which is coagulated to clog the needle;

said reservoir including: an upper adapter upwardly connected to the intravenous container for directing therein the medical liquid in the container, a lower adapter downwardly connected to the delivery tube for discharging the liquid into the tube, the diaphragm formed in a lower portion of the reservoir separating an upper chamber formed in an upper portion of the reservoir and a lower chamber positioned in a lower portion of the reservoir, with said diaphragm formed with a central valve opening in a central portion of the diaphragm and a valve seat formed on the diaphragm disposed around the opening and engageable with the valve for closing the opening; and said floatable valve including: an upper valve portion slidably held in the upper chamber above the diaphragm of the reservoir, a lower valve portion slidably held in the lower chamber below the diaphragm, a stem having a height larger then a thickness of the diaphragm connecting the upper valve portion and the lower valve portion and slidably held in the valve opening in the diaphragm, and a passage formed in the stem and in the lower valve portion when floatably opening the valve for directing medical liquid downwardly through the passage towards the lower chamber and the delivery tube connected to the needle.

2. A dripping apparatus according to claim 1, wherein said passage of the valve includes a vertical slot longitudinally formed in the stem of the valve and a horizontal groove transversely recessed in an upper surface of the lower valve portion and communicating the vertical slot in the stem, with the vertical slot being ended its upper slot end adjacent to and without upwardly exceeding a bottom surface of the upper valve portion.

3. A dripping apparatus according to claim 1, wherein said upper valve portion has a volume and a weight greater than that of the lower valve portion to ensure a gravitational descending of the valve downwardly for closing the valve opening when the upper chamber has no liquid level existing therein.

4. A dripping apparatus according to claim 1, wherein each said valve portion of said valve is formed as semispherical shape, with the upper valve portion arcuately tapered upwardly and with the lower valve portion arcuately tapered downwardly.

* * * * *